US011998355B2

(12) United States Patent
Coakley et al.

(10) Patent No.: US 11,998,355 B2
(45) **Date of Patent: *Jun. 4, 2024**

(54) PRESSURE SENSOR INTEGRATION INTO WEARABLE DEVICE

(71) Applicant: Fitbit, Inc., San Francisco, CA (US)

(72) Inventors: Brett Adam Coakley, San Diego, CA (US); Peter Colin Dess, Pleasant Hill, CA (US); Daniel Joel Freschl, Berkeley, CA (US); Lindsey Michelle Sunden, San Francisco, CA (US); Suraj Gowda, Berkeley, CA (US); Tracy Norman Giest, Oakland, CA (US); Aditya Vivekanand Nadkarni, Emeryville, CA (US)

(73) Assignee: FITBIT, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/311,762

(22) Filed: May 3, 2023

(65) Prior Publication Data

US 2023/0270387 A1 Aug. 31, 2023

Related U.S. Application Data

(63) Continuation of application No. 16/457,419, filed on Jun. 28, 2019.

(51) Int. Cl.
*A61B 5/00* (2006.01)
*A61B 5/01* (2006.01)
(Continued)

(52) U.S. Cl.
CPC .............. *A61B 5/6843* (2013.01); *A61B 5/01* (2013.01); *A61B 5/02438* (2013.01);
(Continued)

(58) Field of Classification Search
CPC ..... A61B 5/6843; A61B 5/01; A61B 5/02438; A61B 5/14552; A61B 5/332; A61B 5/681;
(Continued)

(56) References Cited

U.S. PATENT DOCUMENTS

| | | | | |
|---|---|---|---|---|
| 10,874,348 B1 * | 12/2020 | Han | | A61B 5/6843 |
| 2018/0064397 A1 | 3/2018 | Horikawa et al. | | |

(Continued)

*Primary Examiner* — Eric F Winakur
*Assistant Examiner* — Abid A Mustansir
(74) *Attorney, Agent, or Firm* — DORITY & MANNING P.A.

(57) ABSTRACT

The accuracy of physiological data measured through contact with skin can be validated by characterizing the forces at the surfaces where data is measured. Conventional devices do not monitor the fit of skin-based sensors, making the accuracy and confidence in physiological data dependent on the user ensuring that the device is fitted properly. Over time, the seating of a device will vary due to changes in user activity and the need to periodically remove a device. Inevitably, instances will arise where the device is not fitted correctly, which may result in skewed physiological metrics. By monitoring the forces acting on the housing of a device, the interface of skin sensors can be characterized allowing for confidence metrics in the corresponding physiological data to be determined. In some cases, a user can be notified when a device is not seated properly, and in some cases, data may even be calibrated based on the fit of a device.

20 Claims, 10 Drawing Sheets

(51) Int. Cl.
*A61B 5/024* (2006.01)
*A61B 5/1455* (2006.01)
*A61B 5/332* (2021.01)

(52) U.S. Cl.
CPC .......... *A61B 5/14552* (2013.01); *A61B 5/332* (2021.01); *A61B 5/681* (2013.01); *A61B 5/684* (2013.01); *A61B 5/7221* (2013.01)

(58) Field of Classification Search
CPC ... A61B 5/684; A61B 5/7221; A61B 5/02416; A61B 5/6844
See application file for complete search history.

(56) References Cited

U.S. PATENT DOCUMENTS

| | | | |
|---|---|---|---|
| 2019/0090756 | A1 | 3/2019 | Lu et al. |
| 2020/0077904 | A1 | 3/2020 | Kang et al. |
| 2020/0085320 | A1 | 3/2020 | Kwon et al. |

* cited by examiner

PRESSURE SENSOR INTEGRATION INTO WEARABLE DEVICE

PRIORITY CLAIM

The present application is a continuation of U.S. patent application Ser. No. 16/457,419 entitled "PRESSURE SENSOR INTEGRATION INTO WEARABLE DEVICE" and having a filing date of Jun. 28, 2019. Applicant claims priority to and the benefit of such application and incorporates such application herein by reference in its entirety.

TECHNICAL FIELD

This disclosure relates to the field of wearable devices, and particularly to techniques for validating biometric sensor data associated with such wearable devices.

BACKGROUND

Wearable devices such as watches often have biometric sensors that measure physiological metrics such as a user's heart rate via skin contact. To provide accurate biometric data, wrist-worn devices and other wearables need to be fitted properly so that contact between the user's skin and the one or more sensors of the device is maintained. For instance, if a wrist-worn device is fitted too loosely, it may slide on a user's wrist and lose the skin contact needed to provide accurate data. Many users are unaware that the fitting of their wearable device may impact the accuracy of measured biometric data. Athletes who rely on accurate data for training purposes and may switch to a using a different device if they perceive that measured data is inaccurate. In some cases, an improperly fitted device may provide biometric data indicating a health risk to a user—resulting in unnecessary concern on the part of the user. Worse yet, a sensor might erroneously indicate a healthy physiological response when a user is experiencing severe symptoms and should seek medical attention. All cases in which sensors provide inaccurate data are found unacceptable to users.

Often sensors may be sensitive to an applied pressure keeping the sensor in contact with the user's skin. For example, optical sensors such as photoplethysmography (PPG) sensors measure the total reflectance of blood to estimate changes in blood volume (pulse). If the pressure of the device against skin fluctuates during the measurement, it can push blood out of the capillary bed, which affects the mechanism that the sensor is trying to measure. Other contact-based sensors, like skin temperature and electrode-based sensors, rely on consistent contact area, which is affected by fluctuating pressure. Unfortunately, pressure fluctuations occur regularly during normal wear, as changes in hand position, or even finger position, change the diameter of your wrist and pull and push the device away from your skin.

BRIEF DESCRIPTION OF THE DRAWINGS

Various embodiments in accordance with the present disclosure will be described with reference to the drawings, in which.

During the course of this description, like numbers may be used to identify like elements according to the different figures that illustrate the various exemplary embodiments. It is to be understood by any skilled in the art that the methods described below can be implemented on a computing device employing software modules and one or more processors and that the terms method, process, step, and action can be used to describe events occurring in one or more software modules implemented on a computing device.

DETAILED DESCRIPTION

Systems and methods in accordance with various embodiments of the present disclosure may overcome one or more of the aforementioned and other deficiencies experienced in conventional approaches to measuring biometric data. In particular, various embodiments provide a means of determining whether a user properly wears a device with one or more biometric sensors. In some cases, embodiments provide a means of determining or improving the signal quality of biometric sensors on a wearable device.

In some embodiments, in response to a determination that the contact between a biometric sensor and the skin of a user is problematic, various corrective actions may be taken. For instance, a user may be notified that the wearable device is not fitted correctly. In some cases, a user may be provided with instructions, to, e.g., tighten, loosen, or in some other way adjust the fitting of a device. In some cases, analog or digital signals produced by one or more biometric sensors on the wearable device can be adjusted to improve the accuracy of corresponding monitored biometric data. For instance, analog or digital signals or data may be dependent on the interface between the respective sensor and the skin of the user and thus can be corrected based on factors including a pressure between the wearable device and the skin of a user. In some cases, the biometric data recorded by the wearable device may be unreliable due to a poor fitting of the device. Responsive to a determination of a sub-optimal fit, biometric data may be flagged or may not be recorded until the fitting of the device is corrected. By flagging or removing suspect biometric data, a more accurate representation of physiological metrics can be presented to a user.

Other embodiments described herein pertain to wearable devices capable of monitoring advanced physiological metrics that can be inferred or determined by a combination of physiological metrics. For instance, in some cases, new circulatory metrics can be determined using the morphology of a heart rate signal (e.g., as measured with a PPG sensor) in combination with a known pressure at which the heart rate sensor contacts the user's skin.

Figure 1A:
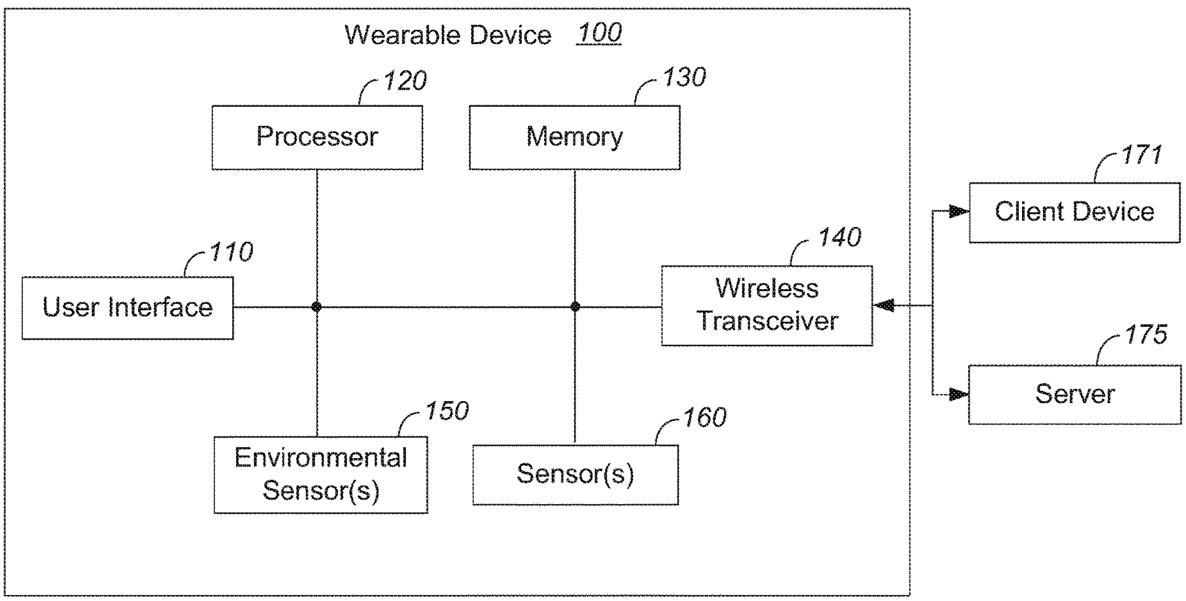
FIG. 1A is a block diagram illustrating an example wearable device in accordance with some aspects of this disclosure.

FIG. 1A is a block diagram illustrating an example wearable device in accordance with aspects of this disclosure. The wearable device 100 may include a processor 120 (which may be a set of processors), a memory 130, a wireless transceiver 140, and one or more sensor(s) 160, including skin-based sensors. The wearable device 100 may also optionally include a user interface 110 and one or more environmental sensor(s) 150. The wireless transceiver 140 may be configured to wirelessly communicate with a client device 171 and/or server 175, for example, either directly or when in range of a wireless access point (not illustrated) (e.g., via a personal area network (PAN) such as Bluetooth pairing, via a wireless local area network (WLAN), via wide area network (WAN), etc.). Each of the memory 130, the wireless transceiver 140, the one or more sensor(s) 160, the user interface 110, and/or the one or more environmental sensor(s) 150 may be in electrical communication with the processor 120. The client device 171 may be a smartphone, a tablet, or another mobile device executing software (e.g., a mobile application) configured to perform one or more techniques described herein. The server 175 may be implemented using one or more computing devices executing software configured to perform one or more techniques described herein. The techniques described herein may be performed by the wearable device 100, the client device 171, and the server 175 in a distributed manner. The wearable device 100 (sometimes referred to as a wearable activity tracker) may be any of a smartwatch, a watch, a wrist-wearable fitness-, health-, or activity-monitoring device, and the like, although the concepts described herein may be implemented on any type of portable or wearable devices including one or more sensors.

The memory 130 may store instructions for causing the processor 120 to perform certain actions. The sensors 160 include at least one biometric sensor at least one fit sensor and may include sensors classified as optical sensors (e.g., a photoplethysmographic (PPG) sensor), motion sensors or inertial sensors (e.g., accelerometer, gyroscope, digital compass, etc.), barometric sensors (e.g., altimeter, etc.), geolocation sensors (e.g., GPS receiver), pressure sensors, force sensors, and/or other sensor(s). Further information regarding such sensors are described in more detail below (e.g., in connection with FIG. 1B).

The wearable device 100 may collect one or more types of physiological and/or environmental data from the one or more sensor(s) 160, the one or more environmental sensor(s) 150, and/or external devices and communicate or relay such information to other devices (e.g., the client device 171 and/or the server 175), thus permitting the collected data to be viewed, for example, using a web browser or network-based application, such as for an individual account or shared account, or shared via social media where permitted or approved by the user. As used herein, the term "collect," in addition to having its ordinary meaning, may be used interchangeably with "determine," "extract," "calculate," "generate", etc. to refer to the steps performed to arrive at the desired data (e.g., breathing disturbance metrics). For example, while being worn by the user, the wearable device 100 may perform biometric monitoring via calculating and storing the user's step count using the one or more sensor(s) 160. The wearable device 100 may transmit data representative of the user's step count to an account on a web service (e.g., fitbit.com), computer, mobile phone, and/or health station where the data may be stored, processed, and/or visualized by the user. The wearable device 100 may measure or calculate other physiological metric(s) in addition to, or in place of, the user's step count. Such physiological metric(s) may include, but are not limited to: energy expenditure, e.g., calorie burn; floors climbed and/or descended; heart rate; heartbeat waveform; heart rate variability; heart rate recovery; respiration, oxygen saturation ($SpO_2$), blood volume, blood glucose, skin moisture and skin pigmentation level, location and/or heading (e.g., via a GPS, global navigation satellite system (GLONASS), or a similar system); elevation; ambulatory speed and/or distance traveled; blood pressure; blood glucose; skin conduction; skin and/or body temperature; electrodermal activity; muscle state measured via electromyography; brain activity as measured by electroencephalography; weight; body fat; caloric intake; nutritional intake from food; medication intake; sleep periods (e.g., clock time, sleep phases, sleep quality and/or duration); pH levels; hydration levels; respiration rate; and/or other physiological metrics.

The wearable device 100 may also measure or calculate metrics related to the environment around the user (e.g., with the one or more environmental sensor(s) 150), such as, for example, barometric pressure, weather conditions (e.g., temperature, humidity, pollen count, air quality, rain/snow conditions, wind speed), light exposure (e.g., ambient light, ultra-violet (UV) light exposure, time and/or duration spent in darkness), noise exposure, radiation exposure, and/or magnetic field. Furthermore, the wearable device 100 (and/or the client device 171 and/or the server 175) may collect data from the sensor(s) 160 and/or the environmental sensor (s) 150, and may calculate metrics derived from such data. For example, the wearable device 100 (and/or the client device 171 and/or the server 175) may calculate the user's stress or relaxation levels based on a combination of heart rate variability, skin conduction, noise pollution, and/or sleep quality. In another example, the wearable device 100 (and/or the client device 171 and/or the server 175) may determine the efficacy of a medical intervention, for example, medication, based on a combination of data relating to medication intake, sleep, and/or activity. In yet another example, the wearable device 100 (and/or the client device 171 and/or the server 22) may determine the efficacy of an allergy medication based on a combination of data relating to pollen levels, medication intake, sleep and/or activity. These examples are provided for illustration only and are not intended to be limiting or exhaustive.

Figure 1B:
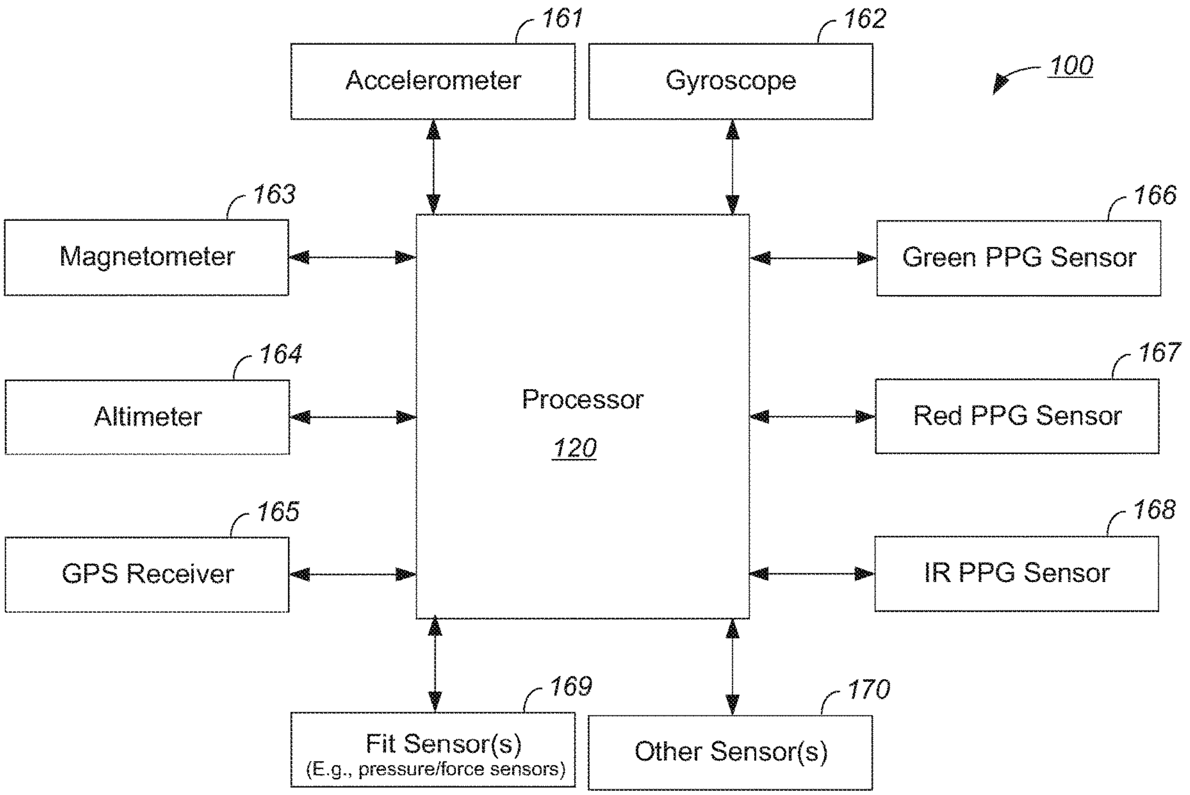
FIG. 1B is a block diagram illustrating sensors that may be included in a wearable device.

FIG. 1B is a block diagram illustrating a number of example sensors that may be included in the wearable device 100 in accordance with aspects of this disclosure. For example, in the embodiment of FIG. 1B, the wearable device 100 includes an accelerometer 161 (e.g., a multi-axis accelerometer), a gyroscope 162, a magnetometer 163, an altimeter 164, a GPS receiver 165, a green PPG sensor 166, a red PPG sensor 167, an infrared (IR) PPG sensor 168, a fit sensor 169, and one or more other sensors 171 (including but not limited to, e.g., a temperature sensor, sensors related to electrocardiography (ECG), electrodermal activity (EDA), etc., an ambient light sensor, a galvanic skin response (GSR) sensor, a capacitive sensor, a humidity sensor, a sound sensor, a force sensor, a multi-axis accelerometer, a gravity sensor, a piezoelectric film sensor, a rotation vector sensor, etc.), all of which may be in communication with the processor 120. Each of the sensors illustrated in FIG. 1B may be in electrical communication with the processor 120. The processor 120 may use input received from any combination of the sensors in detecting the start of an exercise and/or in tracking the metrics for the exercise. One or more of the sensors described herein may not be within the wearable device 100. For example, these sensors may be placed on the chest of the user, the mattress or bedside table of the user, while the wearable device 100 is worn by the user.

Although the example of FIG. 1B illustrates sensors 161-170, in other embodiments the wearable device 100 may include a fewer number of sensors and/or any other subsets and combinations of the sensors. The wearable device 100 may also include one or more additional sensors not illustrated in FIG. 1B.

Additionally, in some implementations a GPS receiver 165 may be located in the client device 171 rather than the wearable device 100. In these implementations, the processor 120 may wirelessly communicate with the client device 171 to control and/or receive geolocation data from the GPS receiver 165 and/or other geolocation sensor(s).

In related aspects, the processor 120 and other component(s) of the wearable device 100 (e.g., shown in FIGS. 1A and 1B) may be implemented using any of a variety of suitable circuitry, such as one or more microprocessors, application specific integrated circuits (ASICs), field programmable gate arrays (FPGAs), discrete logic, software, hardware, firmware or any combinations thereof. When the techniques are implemented partially in software, a device may store instructions for the software in a suitable, non-transitory computer-readable medium and execute the instructions in hardware using one or more processors to perform the techniques of this disclosure. In further related aspects, the processor 120 and other component(s) of the wearable device 100 may be implemented as a System-on-Chip (SoC) that may include one or more central processing unit (CPU) cores that use one or more reduced instruction set computing (RISC) instruction sets, a GPS receiver 165, a wireless wide area network (WWAN) radio circuit, a WLAN radio circuit, and/or other software and hardware to support the wearable device 100.

The wearable device 100 may comprise one or more optical or electro-optical sensors, such as, for example, one or more PPG sensors. The PPG sensor(s) of the wearable device 100 (e.g., green PPG sensor 166, red PPG sensor 167, IR PPG sensor 168, etc.) may generate PPG data usable to calculate heart rate, heart rate variability, respiration rate, and/or oxygen saturation, among other things. PPG data can be used to calculate a user's heart rate by measuring the time between peaks or by calculating a dominant frequency in the optical signal.

In various embodiments, the PPG sensors described herein may include one or more electronic semiconductor light sources, such as LEDs, or other light sources that produce light using any of filaments, phosphors, or laser. In some implementations, each light source of the wearable device 100 emits light having the same center wavelength or within the same wavelength range. In other cases, at least one light source may emit light having a center wavelength that is different from another light source. The center wavelengths of the light emitted by the one or more light sources may be in the range of 495 nm to 570 nm. For example, a particular green light source may emit light with a center wavelength of 525 nm (or approximately 525 nm). In other embodiments, one or more light sources may emit red light (e.g., 660 nm or approximately 660 nm center wavelength), and one or more light sources may emit IR light (e.g., 940 nm or approximately 940 nm center wavelength). In some embodiments, independent control of all light sources is provided. In other embodiments, several light sources are controlled together as a gang or bank.

The PPG sensors described herein may include one or more light detectors adapted to detect wavelengths of light emitted from light sources, including those reflected or passed through elements that may impact the wavelengths or other aspects of the light. One or more PPG sensors described herein may include a single light source and a single light detector. Alternatively, other PPG sensors described herein may include multiple light sources and/or multiple light detectors. A light detector, in an embodiment, may comprise one or more detectors for detecting each different wavelength of light that is used by the light sources. For example, a first detector may be configured to detect light with a wavelength of 660 nm (or approximately 660 nm), a second detector may be configured to detect light with a wavelength of 940 nm (or approximately 940 nm), and a third detector may be configured to detect light with a wavelength of 525 nm (or approximately 525 nm). Examples include photodiodes fabricated from semiconductor materials and having optical filters that admit only light of a particular wavelength or range of wavelengths. The light detectors may comprise any of a photodiode, phototransistor, charge-coupled device (CCD), thermopile detector, or complementary metal-oxide-semiconductor (CMOS) sensor. One or more of the light detectors may comprise a bandpass filter circuit.

Figure 2A:
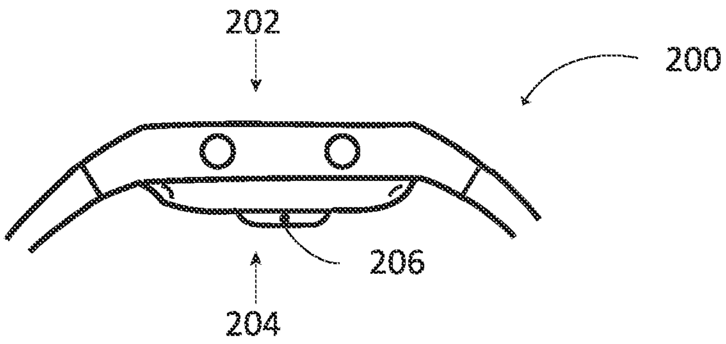
FIGS. 2A-2C illustrate the fitting of a wrist-worn device on a user.
Figure 2B:
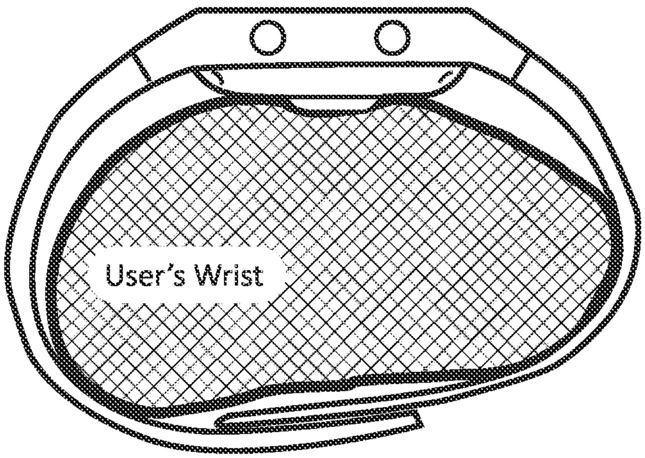
Figure 2C:
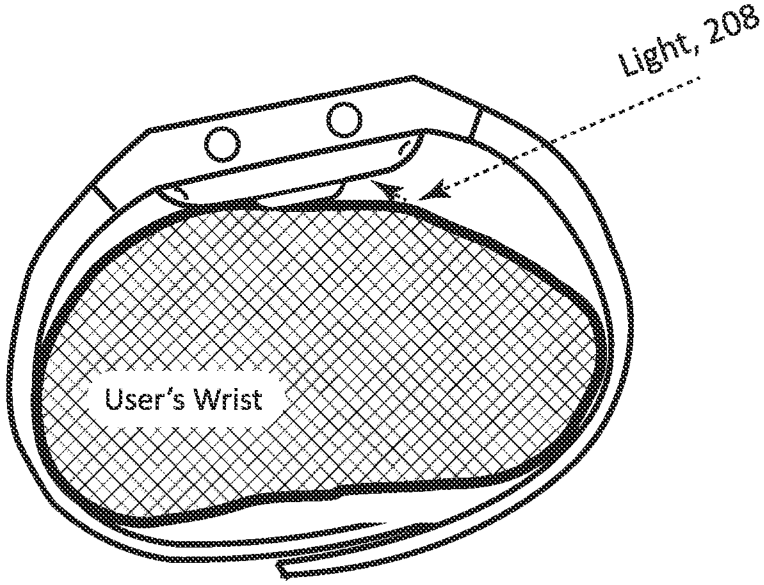

The accuracy of data provided by biometric sensors such as PPG sensors and other sensors that require direct contact with the skin can be affected by how a user wears the wearable device. As used herein, the term skin sensor is used to refer to all sensor types that depend on skin contact to measure a physiological metric. Skin sensors generally perform optical sensing or electrical sensing and can measure parameters such as a user's heart rate or body temperature. FIGS. 2A-2C illustrate how the fit of a wearable device, and in particular the seating of a skin-based sensor, can significantly affect the accuracy of data collected by the device.

FIG. 2A depicts a side view of a wrist-worn device 200 having a top surface 202, which may have a display unit (not shown), and a bottom surface 204 which may comprise one or more skin sensors 206 (e.g., a PPG sensor). While skin sensor 206 is depicted on the bottom surface of the device, skin sensors can be placed at any location of a wearable device in direct contact with the skin of a user. For example, on a wrist-worn device, a skin sensor might be included anywhere on the strap of the device that makes contact with the skin of the user. In some cases, a skin sensor might be worn separately from the wearable device and may transmit data wirelessly by Bluetooth or another wireless protocol.

FIGS. 2B and 2C depict wearable device 200 of FIG. 2A being worn on the wrist of a user. FIG. 2B depicts device 200 being worn in a manner such that skin sensor 206 has good contact with the skin on the user's wrist. In contrast, FIG. 2C depicts an example where skin sensor 206 is only partially in contact with the user's skin. This could be, e.g., a result of the device being worn too loosely or being seated improperly—for instance, the bottom surface 204 may be seated on the head of the ulna bone which may reduce the area of the sensor in contact with the user and consequentially the quality of a signal produced by the skin sensor.

An improper fit of the wearable device can lead to a poor or incoherent signal from the skin-based sensor. For instance, if the sensor is an optical sensor, such as PPG sensor, data produced by the sensor may be affected by ambient light or by changes in reflectance and absorbance caused by movement of the sensor in relation to the user's skin. When a wrist-worn device is used to record biometric data during, e.g., running or walking, periodic movement of the device in relation to the skin of the user may be reflected in the measured biometric data. While the above example pertains to an optical sensor, such as an optical PPG sensor, similar effects occur with other skin sensors such as electrode base sensors. While not depicted, the accuracy of biometric readings may also be affected if a wearable sensor is fitted too tightly. For instance, if a wrist-worn device is worn too tightly, capillaries may be constricted which may change the waveform detected by an optical heart rate sensor.

Figure 3:
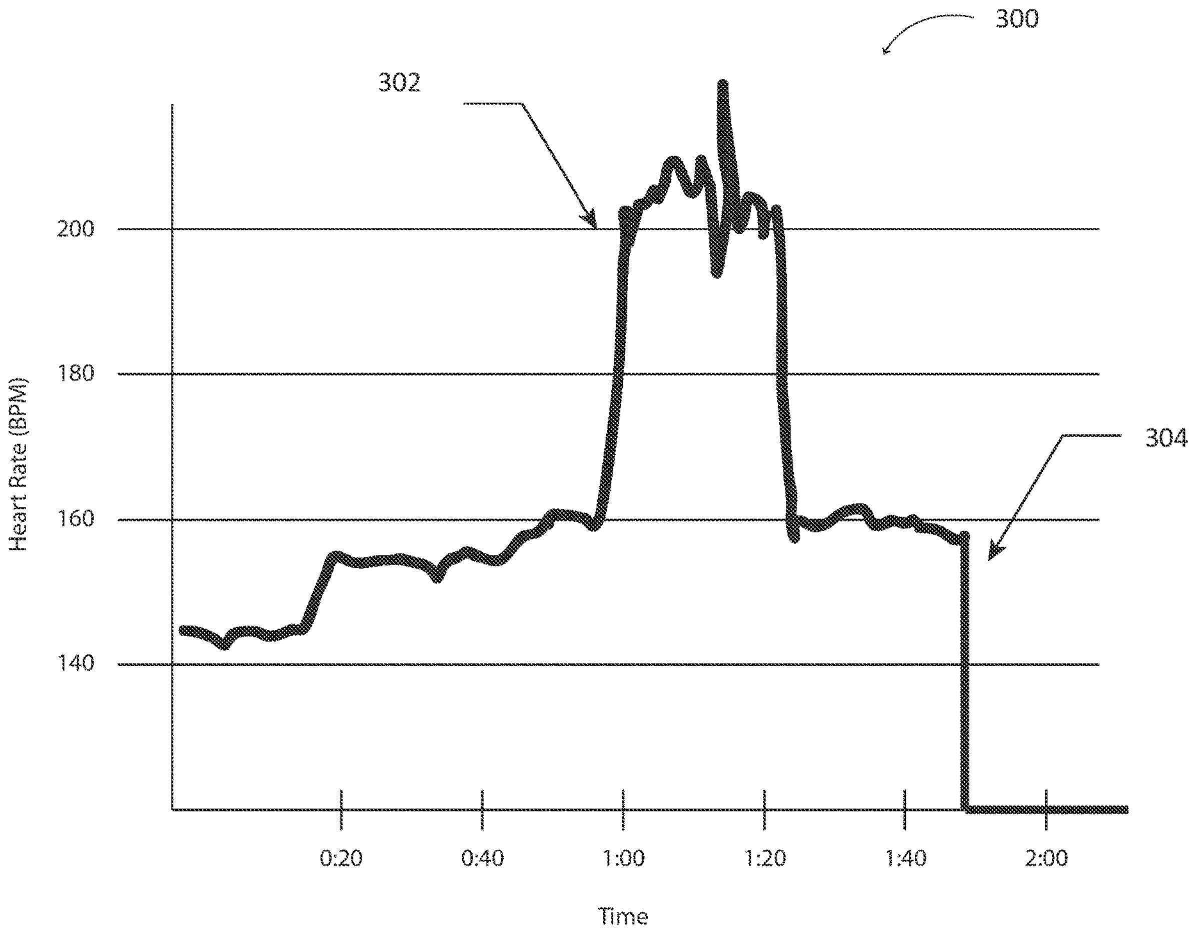
FIG. 3 depicts heart rate data provided by poorly fitted skin sensor.

FIG. 3 illustrates an example of poor heart rate data resulting from the improper seating of a skin sensor against the skin of a user. Plot 300 provides the heart rate data of the user during a recorded activity. Such plots may be presented to a user through an application on an accompanying client device or through a website to which the activity data can be uploaded. In the depicted example, a user might expect to see heart rate data in the range of about 140 beats per minute and 170 beats per minute (e.g., possibly corresponding to a run or a bike ride). When reviewing an activity, a user might quickly be able to identify portions of bad data such as the data beginning at 302 which might be well above the user's maximum heart rate, and the data beginning at 304 where no heart rate data was recorded. Occurrences inaccurate heart rate data might be caused by an optical or electrode-based heart rate sensor that is seated poorly against the user's skin. For instance, an electrode based heart rate sensor may be worn loosely, such that it is affected by vibration (e.g., wind vibration) leading to the unusually high heart rate data at 302 and later loses contact and fails to record a signal at 304. While it may be obvious what portions of data are inaccurate as depicted in FIG. 3, in some cases, a poorly seated sensor many result data inaccuracies that still fall within a conceivable range, e.g., within 5% or 10% of the actual value. While such data might go unnoticed if only a rare occurrence, over time users may begin to question biometric data the device produces.

In embodiments described herein, wearable devices are equipped with one or more fit sensors to characterize the fit of a wearable device. Each of the one or more fit sensors records data which collectively is referred to herein as a fit signature. The fit signature can be used to characterize the interface between skin sensors and the skin of the user. In some cases, the fit signature is used to characterize the placement or orientation of the wearable device on the user. A fit sensor can be any deflection, force, pressure, or strain based sensor that can be used to characterize the interface between the wearable device and the skin of a user. In many cases, these sensors are Micro-Electro-Mechanical System (MEMS) based sensors that are attached to the housing of the device. Fit sensors may include piezoelectric sensors, piezoresistive sensors, strain gauges (e.g., resistive, capacitive, inductive and ultrasonic-based strain gauges), load cells, pressure sensors and the like. The sensors measure a force, a contact pressure, or a strain experienced by the housing of the wearable device. Data provided by fit sensors can then be used to characterize the interface between skin sensors and the user. For example, by analyzing a fit signature, it can be determined if the wearable device is being worn, if the contact pressure at the interface between the skin of a user is within an acceptable range, and in some cases, the manner in which the wearable device is being worn. In some cases, the use of fit sensors enables the contact of a device's housing against a user's skin to be characterized using a two-dimensional grid or map. Characterizing this interface can, e.g., allow for intelligent sensor selection in cases where multiple biometric skin sensors are used. For example, it may be determined that a first PPG sensor has better skin contact than a second PPG sensor located at a different position of the device. In such cases, recorded biometric data may only reflect data provided by the first PPG sensor or, or in some cases, the data provided by each sensor may be weighted based on the fit of the sensor against the user's skin.

Figure 4:
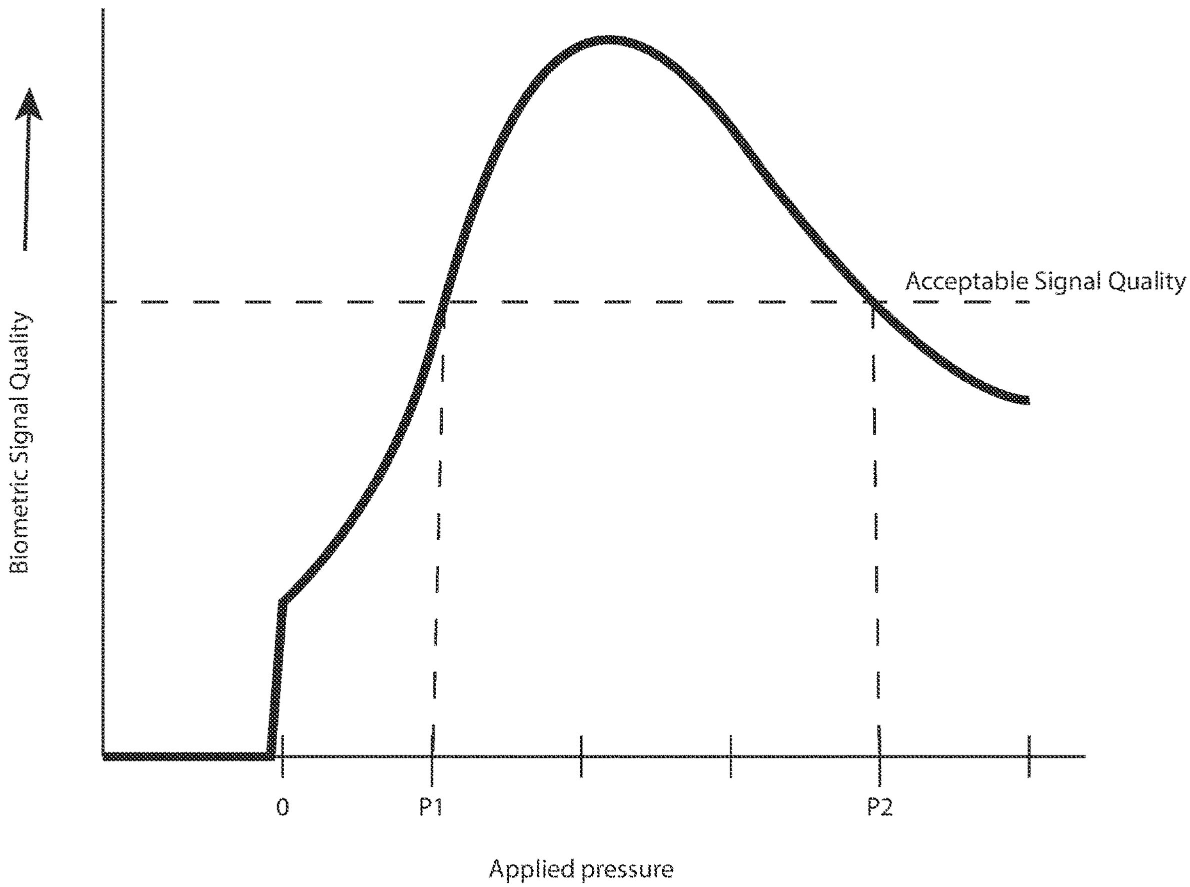
FIG. 4 is a plot illustrating the relationship between the signal quality of a biometric skin sensor and the pressure which the sensor contacts the skin of a user.

FIG. 4 illustrates a relationship between the signal quality provided by a skin biometric sensor and the pressure which the sensor is pressed against the surface of the skin. Typically, there is a range of pressures, e.g., between P1 and P2, where skin sensors can accurately and reliably record biometric data. At low pressures (e.g., below P1), a skin sensor may have a poor seating on the skin of a user. For example, at pressures below P1, the sensor may slide, rock, or otherwise fail to maintain sufficient contact for accurate measurements. At high pressures (e.g., above P2), deformation of the bodily tissue such as the constriction of capillaries may also lead to poor data. In some cases, the pressure at which a sensor is applied to the skin of a user can be related to a confidence value in the measured biometric data. In some cases, a determined confidence value may further depend on other metrics such as a signal to noise ratio, measured body temperature, ambient temperature, humidity, and/or physiological metrics of the user.

It is recognized that factors including the type of skin sensor (e.g., optical or electrode based), the placement of the sensor on a wearable device, and the physiological makeup of a user may impact the relationship between the contact pressure at the sensor and signal quality. For instance, due to greater compliance in skin tissues, sensors may produce reliable data over a broader range of pressures for users reporting a higher body mass index (BMI) values than for users reporting low BMI values. In other cases, differences in skin color, body fat percentage, and hair density can affect the relationship between applied pressure and signal quality.

Figure 6A:
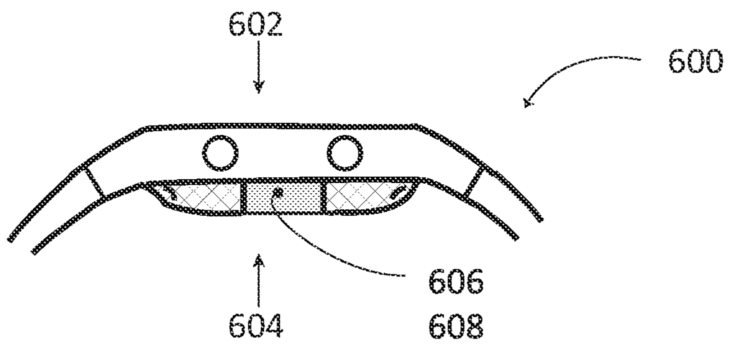
FIGS. 6A and 6B provide examples of how fit sensors may be placed relative to a skin sensor on a wearable device.

In some cases, a fit sensor such as a strain gauge or a force sensor is placed immediately adjacent to a biometric skin sensor in the housing of a wearable device. FIG. 6A depicts a side view of a wrist-worn device 600 having a top surface 602, which may have a display unit (not shown), and a bottom surface 604 which may one or more skin sensors 606 (e.g., a PPG sensor). In some cases, fit sensor 608 may be directly mounted between the housing of the device and the skin sensor, such that microscopic motion of the skin sensor relative to the housing can be determined. In some embodiments, a fit sensor may measure a deflection in the housing of the wearable device at or near the location of the skin based sensor. From a deflection in the housing, the forces on the skin sensor can then be determined or estimated. Fit sensors are generally mounted to a glass or metal backing or another rigid component of the device housing. In some cases, a fit sensor is part of the same module as a skin sensor. Generally, sensors that are substantially linear over a range of expected loads are preferred. In some instances, fit sensors may be mounted to an elastic material in the housing or in a band associated with the device. As sensors configured for measuring large displacements may be non-linear, some form of signal or data calibration may be needed.

Using the geometry and the construction of the wearable device, deflection measurements recorded by a fit sensor can be correlated to the contact pressure of a skin sensor that is also mounted to the housing of the device. The relationship between data provided by a fit sensor and the pressure at a skin sensor can be determined empirically through testing or methods such as a finite element analysis using a model of the wearable device. In some cases, a table or function can be created that maps data provided by the fit sensor (e.g., force, deflection, etc.) to the pressure between the skin sensor and the user's skin.

In some cases, a wearable device can have multiple fit sensors such as depicted in 6*b* where fit sensors 608*a* and 608*b* are placed on the sides of skin sensor 606. By including multiple sensors, the confidence in the fit data and consequentially the sensed biometric data can be improved. In some cases, such as when multiple fit sensors are placed on the back of a wrist-worn device, the data provided by each sensor can be averaged to estimate a pressure on a skin based sensor. In some cases, the measurements provided by a plurality of fit sensors can be used to determine or estimate a contact pressure at the location of a skin sensor or at another contact location of the device housing.

Figure 6B:
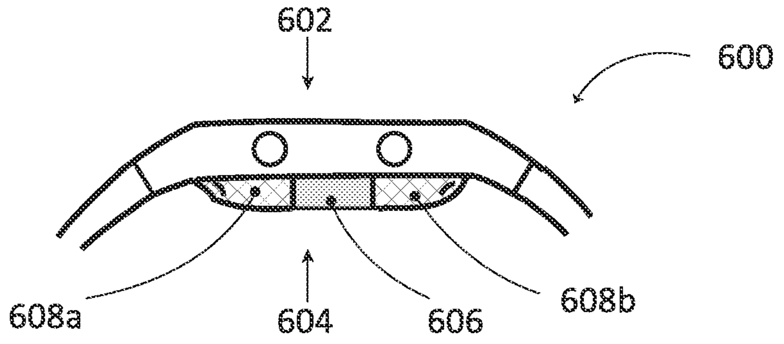
Figure 6C:
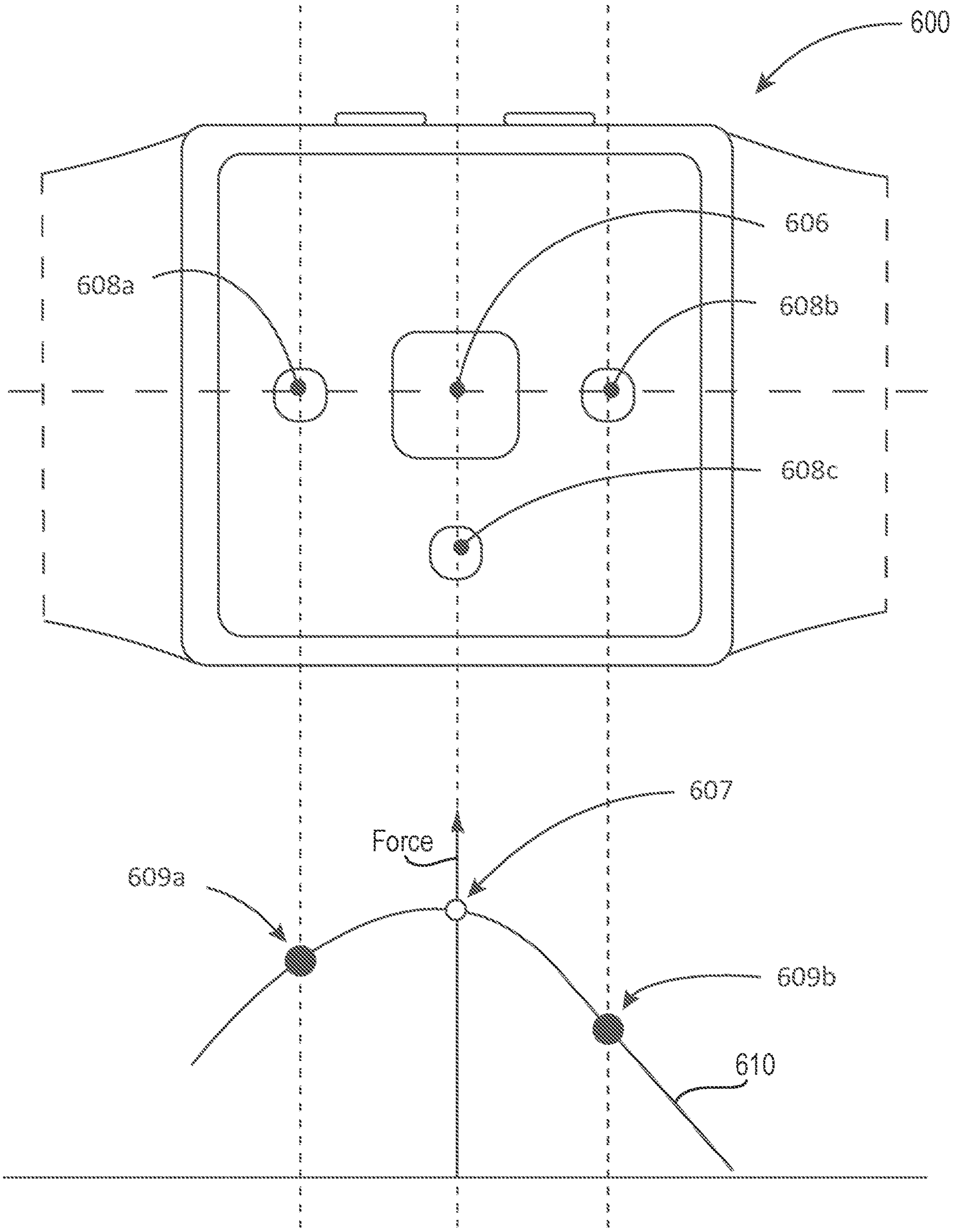
FIG. 6C is used to illustrate some configurations of a fit signature in which data collected at one or more fit sensors can be used to characterize the forces at the interface of a skin sensor and the skin of a user.

FIG. 6C depicts the bottom surface of a wrist-worn device, such as the wrist-worn device depicted in FIG. 6B. The device includes a skin sensor 606 and fit sensors 608*a-c*. Using the data provided by the fit sensors (609*a* and 609*b*), the contact force experienced on the surface of the wearable device 607 can be determined. The contact force or the contact pressure at the sensor location may be determined using curve fitting techniques, finite element methods and the like. In some cases, a fit signature may include a determination of the force experienced at various portions of the wearable device such as illustrated by curve 610. In some cases, additional fit sensors such as sensor 608*c* can be used to validate or improve the confidence in the pressures determined at skin sensors. In some cases, such as when three or more sensors are used, the fit signature can determine a mapping of the normal force experienced on a surface of the wearable device. The fit signature can then be used to determine, e.g., the center of force or the center of pressure the surface of the wearable device. By analyzing the forces recorded in a fit signature, the signature can further be used to determine if a device is being worn correctly. For instance, using the skeletal geometry of the human wrist, the fit signature can be used to determine whether a wrist-worn device is seated correctly, whether the device propped up on the head of the ulna bone, or whether the device is being worn at 180 degrees from its intended positioning.

While fit sensors generally measure a deflection or force in a direction that is substantially perpendicular to a surface of the device in contact with the user's skin—this is not necessary. For instance, a fit signature may be augmented by, e.g., tension measurements in the band of a wrist-worn device. In some cases, the data provided by other sensors of the wearable device may also provide data that can be included in the fit signature. For example, a light sensor may be used to help determine whether a user is wearing a device by monitoring for changes in lighting on the back surface of the device. In some cases, inertial data provided by accelerometers and gyroscopes can be used when detecting whether a biometric device is moving with respect to the user, e.g., by detecting a pattern of movement that associated with a loosely fitted device.

Fit data provided by one or more fit sensors can be used to validate the biometric measurements provided by skin sensors. For instance, biometric data measured by skin sensors can be validated when the fit signature includes data that falls within an acceptable range of values. In some cases, acceptable ranges of data in a fit signature may be determined based on a contact pressure at a skin sensor that can be determined based on the data. In some cases, acceptable ranges may be determined through testing, e.g., by comparing the signals or data produced by the skin sensor to another trusted source of data for a variety of data points as recorded by the fit sensor(s). As mentioned, acceptable ranges for a fit signature may depend on, e.g., the type of skin sensor and physiological metrics of the user. In some cases, an acceptable range in the fit signature may be predetermined by the manufacturer. In some cases, a user may be provided with an option to provide various metrics as part of a user profile which may affect what an acceptable range in the fit signature is.

In some cases, confidence values are assigned to measured data based on the fitting of the wearable device. For instance, if a wrist-based device is worn too loosely, no signal may be detected, or an interrupted signal may be detected. If a wrist-based device is worn too tightly, capillary beds may be constricted and alter the waveform of a measured heart rate. Confidence metrics may be used to help users assess the accuracy of their data. In some cases, if a wrist-based device is worn tightly, a pressure sensor may be used to measure the heart rate data as a pressure wave. Acceptable confidence values for heart rate data measured in this manner might require, e.g., at least a threshold amount of contact pressure.

In some cases, fit signatures can be used to calibrate data provided by an optical pulse oximeter (more commonly known as an SpO2 sensor). SpO2 sensors are used to determine oxygen concentration in the blood and can be helpful in diagnosing conditions such as sleep apnea. As with other sensors, data provided by SpO2 sensors may depend in part on the pressure at which the skin sensor is applied to the user's skin. For instance, if a SpO2 skin sensor is pressed too tightly against the user's skin, the sensor may provide data indicative of sleep apnea, when the user may actually just be sleeping in a position that causes pressure to be applied to the device. In some cases, the SpO2 readings can be calibrated in proportion to the applied pressure. If it is determined that the $SpO_2$ measurements are inconclusive and cannot be corrected due to the fit signature, e.g., if it determined that the sensor has lost contact with the skin of the user, the SpO2 data can be thrown out or in some other way marked as suspect so that the user does not put too much weight in data that is likely to be inaccurate.

Figure 5:
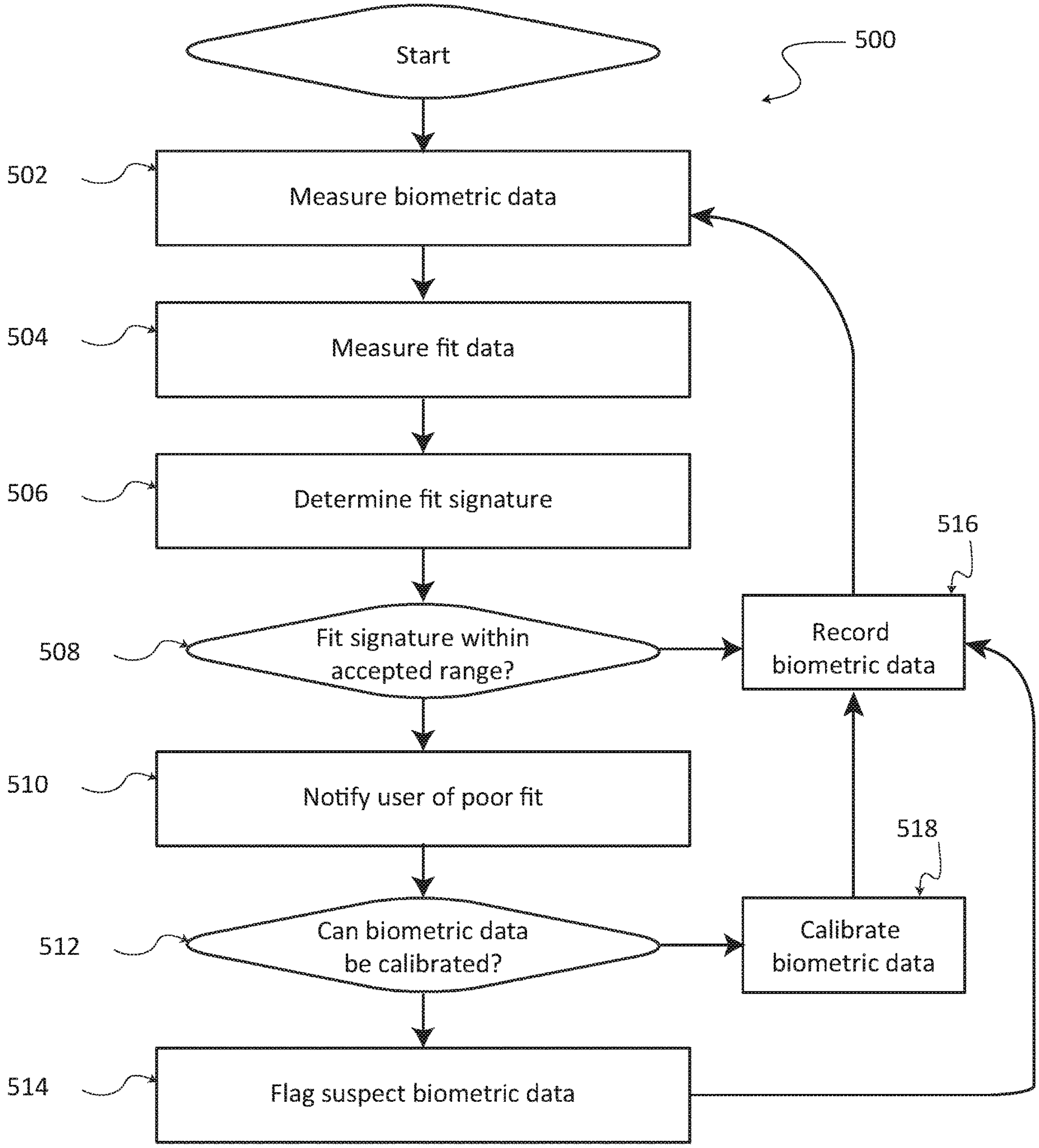
FIG. 5 provides a method for validating biometric data provided by one or more skin sensors of a wearable device.

FIG. 5 provides a method 500 for validating biometric data provided by one or more skin sensors of a wearable device. It should be understood that, for this and other processes discussed herein, there can be additional, fewer, or alternative steps, performed within the scope of the various embodiments unless otherwise stated. In operation 502, biometric data is collected by one or more skin sensors. These skin sensors can be, e.g., electrode or optical sensors that provide data continuously or periodically to a controller of the wearable device. In operation 504, the fit signature is measured using one or more fit sensors of the wearable device. The fit sensors may measure deflection, force, displacement, and other parameters for characterizing the interface between the wearable device and the skin of the user. In operation 506, the data produced by the one or more fit sensors is aggregated to form a fit signature. The fit signature may in some cases be the compilation of fit data, and in some cases, the fit signature may comprise calculated metrics based on the measured fit data such at the contact pressures at fit sensors of the device. In some cases, the fit signature is simplified into a single metric such as a fit score which represents the quality of the interface between the wearable device and the skin of the user. In operation 508, the fit signature is compared to an expected signature or an acceptable range of values provided by the fit signature. If the fit signature is within an acceptable range, then biometric data to when the fit signature was recorded is considered to be valid and designated as an acceptable signal. The data may be recorded in memory or transmitted to a client device for storage 516.

If the fit signature is determined to be outside of an acceptable range, a notification can be provided to the user 512. This notification can be provided visually through a display on the device, audibly through speakers of the device, or, e.g., through a vibration generated by the device. In some cases, the notification can be transmitted to a client device such as a smartphone or tablet associated with the wearable device.

If the fit signature deviates from an acceptable range, it can be determined whether the measured biometric data can be corrected or calibrated. This determination may depend on steady-state conditions are maintained and how for the fit signature deviates from the acceptable range. For instance, if the wearable device becomes unseated while a user is sleeping, and all other inputs indicate that a user has not gotten out of bed, a corrective factor may be applied to heart rate data when the fit signature deviates from an acceptable range. Determining whether biometric data can be calibrated may thus depend on data provided by other sensors of the wearable device including, e.g., motion sensors, temperature sensors, and light sensors.

If it is determined that the data cannot be calibrated, the suspect biometric is flagged 514 (e.g., designated as a sub-optimal signal). When a user views data recorded by the wearable device, e.g., through a display on the device or through an application on an associated client device, the flagged data may be hidden from a user. In some cases, the flagged data is presented to the user but is displayed using a different color with a visual indicator to alert the user that the data suspect data may not be accurate. In some cases, calculated metrics such averaged or normalized biometric data may omit suspect data biometric data which might significantly impact the calculated values. In some instances, suspect data is flagged using the metadata associated with a file containing recorded biometric data. While not depicted, in yet other cases, suspect data outside of an acceptable range is not saved or transmitted to a client device.

Figure 7A:
FIGS. 7A-7D Illustrate how notifications can be provided on a display of a wearable device responsive to a measured fit signature.
Figure 7B:
Figure 7C:
Figure 7D:
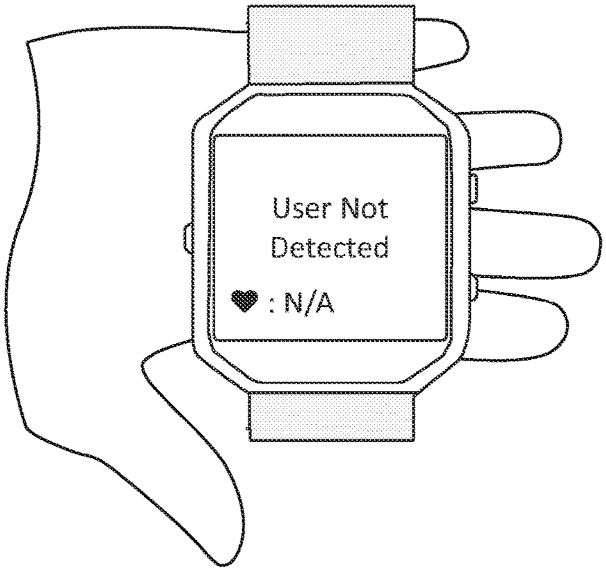

While it may be possible to calibrate bad biometric data resulting from a poor fitting of the biometric device, it is preferable to measure biometric data when the device is fitted properly. As mentioned in method 500 of FIG. 5, one aspect of this disclosure pertains to notifying a user to inform them when the wearable device, specifically skin sensors of the device, are seated improperly on the user's skin such that they cannot accurately or reliably measure biometric data. FIGS. 7A-D depict several examples of notifications that can be provided on a wrist-worn device. In FIG. 7A, a notification is provided to a user to loosen the tension of the wrist-worn device. This may be because the contact pressure at the skin sensors is too high to accurately record biometric data. In some cases, such as when the device has been worn for an extended period of time or when biometric data is not being monitored, the wearable device can suggest loosening the strap or removing the device to allow the user's skin to breath. In some cases, using the fit signature, it can be determined that the device is being worn, but that there insufficient contact pressure at a skin sensor of the device. In this case, an alert may be provided to have the user increase the tension on the strap of the device or otherwise make an adjustment to improve the contact of the skin sensor with the skin of the user. If the device is seated poorly on the user's wrist or, e.g., if a user is wearing the wrist-worn device on top of an article of clothing a notification may instruct the user to adjust the fitting as shown in FIG. 7B. In some cases, specific instructions may be provided to the user for how to correct the fitting of the device. When a user has adjusted to the band tension, the orientation, or the placement of the device such that a fit signature is within the accepted range, an indication can be provided to the user as depicted in FIG. 7C.

In some embodiments, fit signatures and notifications can be used to help a user determine whether an appropriate model of the wearable device is suited for a user. For instance, in the case of wrist-worn devices, various models may have differences including differences in the device profile at the skin interface, differences in the positioning of skin sensors, differences in band length, differences in elasticity, and the like. User's having differing physical characteristics such as differences in wrist size, skin color, hair density, BMI, fat percentage, and the like may find that some models of the wrist-worn device can be fitted better than others. In some cases, a wrist-worn device may be configured to provide a fit score to a user as depicted in FIG. 7C. Providing a fit score can be helpful in improving customer satisfaction. For instance, when a user is looking for a device in a retail store, they can be provided with an objective measure of which device models are suited for their physical makeup and will be able to provide accurate biometric data. Similarly, customers who purchase a device online can be provided with a metric informing them whether a device fits or should be exchanged for a different model.

In addition to helping users identify device models that fit appropriately, fit signature data can also be helpful in troubleshooting issues measuring biometric data. With conventional devices, customers may become frustrated attempting to describe problems to a remote customer support service representative. If the fit signature can be provided to the customer support representative, the issue may be more quickly diagnosed, since many issues in biometric sensing are simply the result of an improperly fitted device. In some cases, a user may be able to authorize that device data and fit data be provided electronically to a customer support representative. For instance, fit signature and well as other status indicators of the device may be transmitted via Bluetooth to a phone which relays the data to a remote server.

One issue that may arise with conventional wearable devices, it that it can be difficult to confidently determine when a user in an inactive state is wearing a device (e.g., a user who is resting or sleeping) and when the device not being worn at all (e.g., when the wearable device is resting on a nightstand). By analyzing the fit signature, the wearable device can more accurately determine whether or not a device is being worn. In addition to relying on, e.g., displacement and force data, this determination may, in some cases, be based on data provided by skin sensors (e.g., heart rate sensors and temperature sensors), light sensors, inertial sensors, learned user patterns (e.g., a sleep schedule) and the like. By accurately determining whether a device is being worn, the battery life can be extended. For example, some sensors may be turned off entirely or may only record data intermittently to save power. Data provided to a user is also improved. As an example, conventional devices may incorrectly determine that the user had a great night of sleep when the user simply was not wearing their device. By analyzing whether the device is even being worn, some occasions for recording inaccurate data may be avoided.

In some cases, removing a wearable device may change the mode that the device operates. For instance, when a user removes the device, the device may transition to off-wrist mode (or an off-user mode). An off-wrist mode might, e.g., alter the brightness of a display, change the orientation of a display such that it appears right side up when placed on a nightstand, or reconfigure the user interface such that features that are more likely to be accessed in an off-wrist mode are placed in prominent locations. As an example, options for setting an alarm or changing system settings may be accessed more easily through a user interface when the wearable device is in an off-wrist mode. When puts on the wrist-worn device (or another wearable device), the device may transition to an on-wrist mode which may change settings such as increasing the brightness of a display, locking the orientation a user interface provided through a display, and the configuration of interface features.

In some cases, when it is determined that a device should be in an on-wrist mode based on the fit signature, the sampling rate of biometric data is increased. In some cases, biometric data and other activity data is automatically stored locally on a device for a certain period of time, such that if a user forgets to start an activity tracker (e.g., to track a run, a swim, or a bike ride) the relevant data will still be recorded. In some embodiments, a fit signature can be used for exercise or activity detection. For instance, logic on the device may be configured to detect exercise activity when both inertial data is measured, and a fit signature indicates that the user is wearing the device.

In some embodiments, determining if a device is worn by a user can be useful for authentication purposes. Wearable devices may store protected user data and can be used for wireless payment methods. If it is detected that a device has been removed, a user may be requested to verify their identity—e.g., by entering a pin or by providing information through a client device. In some cases, a fit signature along with other data recorded by the device including heart rate data, SpO2 data, learned patterns of user behavior such as stride, cadence, and the like can be used to verify the identity of a user.

By using pressure data included in or derived from a fit signature, new physiological metrics can be determined. As discussed, the data provided by optical sensors such as PPG sensors and SpO2 sensors may depend on the pressure at which these sensors are applied to the skin of a user—however, conventional wearable devices have not associated circulation data with applied pressure. By combining the morphology of heart rate data with fit signature data, advanced circulation metrics can be acquired. Throughout the course of a day, the fit signature and a PPG waveform will vary due to changes in physical activity. For example, exercise increases a user's heart rate causes swelling near the extremities which increases the contact pressure with a wearable device. By monitoring data throughout extended periods of time such as over the course of a day or a month, more information can be determined about the user's circulatory health. For instance, by combining pressure data with the waveform of a PPG sensor, data relating to the viscosity of a user's blood, the elasticity of capillaries near the sensors, and the user's blood pressure can be determined. In some cases, a user's body temperature or skin temperature (e.g., as measured by a temperature sensor on the device) can be used in conjunction with PPG data and pressure data when determining such circulatory metrics. In embodiments, a baseline may be determined for a user. If a change in the user's baseline is detected, a notification may be presented to the user if the change indicates a health risk. In some cases, using pressure data and temperature data collected by the derived, a user's skin perfusion can be characterized. In some cases, the device can be used to identify or ischemia or circulatory disorders like Reynaud's syndrome. In some embodiments, the wearable device may be configured to alert a doctor or the paramedics if certain conditions are met and indicate a health risk.

In some embodiments data in a fit signature can be used to determine a users' heart rate. For instance, when the pressure of the wearable device against the user's skin is sufficient (or in some cases if the fit sensor is highly sensitive), the pulses in heart rate may be detected by changes in contact pressure recorded in the fit signature corresponding to the user's pulse.

Figure 8:
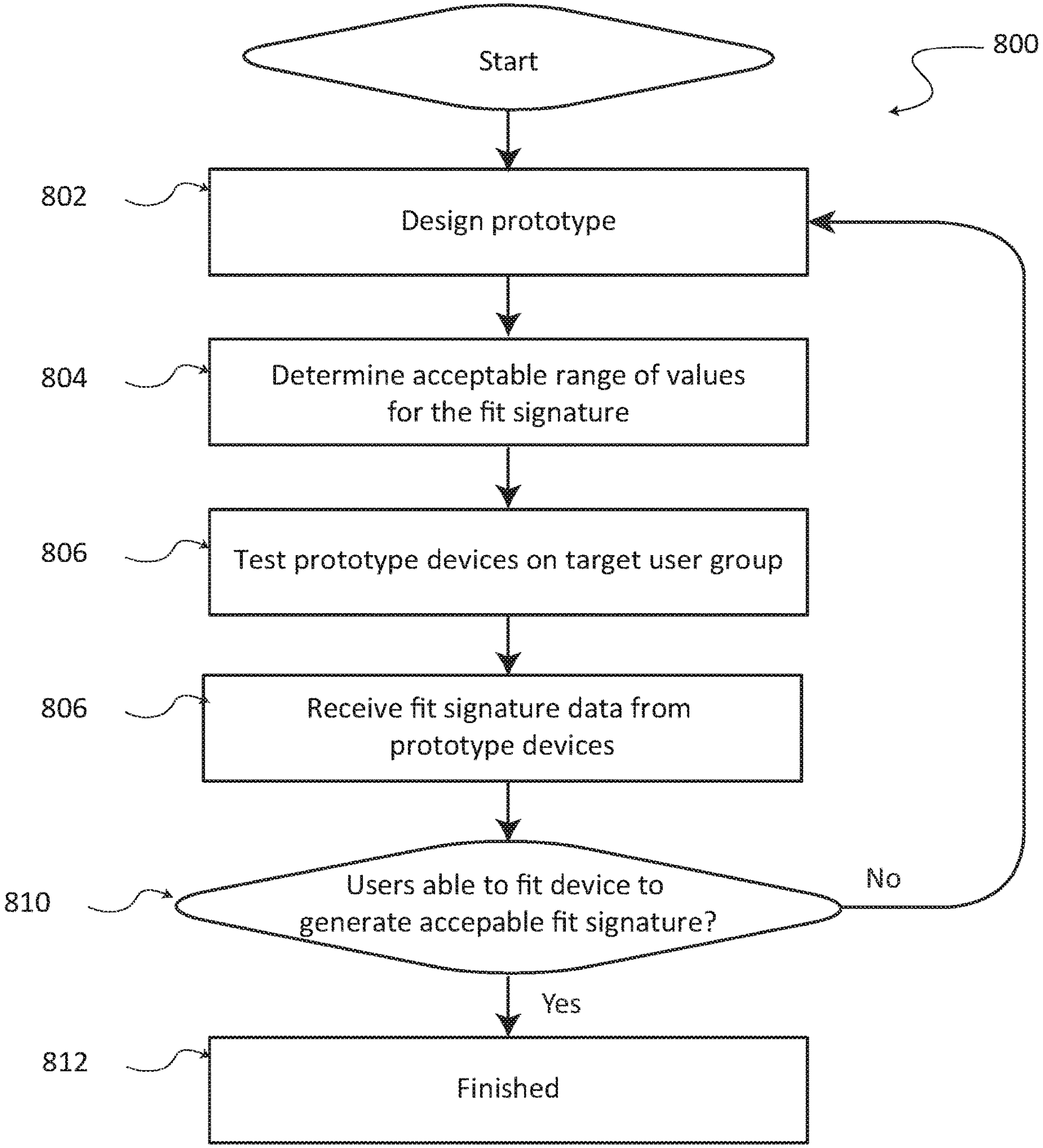
FIG. 8 provides a method for validating and prototyping the designs of wearable devices using fit sensors.

Another aspect of this disclosure pertains to a method 800 for designing and validating a wearable device provided in FIG. 8. The method starts in operation 802 where a model of the device is generated. The model may be a computer-aided design CAD model that includes the housing of the wearable device, biometric sensors, and fitness sensors. In step 804, an acceptable range for a fit signature is determined. Determining an acceptable range for a fit signature can include, e.g., performing a finite element analysis using a CAD model of the device. The ranges of acceptable fit signatures may also depend on the physical characteristics of the user as previously discussed. In operation 806, the device is made and tested on users. In some cases, the housing of units can be 3D printed or otherwise manufactured using a method other than might be used for mass production of a finalized device. In some cases, devices may be tested by users for an extended period so that a variety of physical activities and environmental conditions are recorded. In operation 808, fit signatures are received from the devices. In some cases, a single fit signature is received for each user that tested the device, and in some cases, a history of fit signatures is received spanning the time over which the device was tested. In operation 810 the received fit signatures are analyzed to determine if the design of the device can be properly fitted to a target group of users, which may be, e.g., children of a particular age, adults with slender wrists, or adults having larger wrists. During this analysis, common fit issues are determined, and in some cases mapped to the physical characteristics of the test users. If test users are easily able to fit the device properly so that the fit signature is within a predetermined range, the device can be finalized for production. If there are issues with some users being able to get or maintain a good fit, then a new version of the device can be generated and the process repeated iteratively. If another design iteration is needed, the placement of sensors, materials used for the housing, the materials used for the band, and the geometry of the device including the contours of the device that are in contact with the user may all be adjusted to improve the likelihood that users of the selected audience will be able to comfortably fit the wearable device so as to accurately and reliably record biometric data. While fit signature data can be used when designing and validating prototype devices, fit data may also be collected from devices sold to customers. For example, in some cases, customers may be provided with the option of sharing fit signature data automatically in situations such as when a device is connected to WiFi. In some cases, collected fit signature data can be used to identify areas for improving future products. Collected fit data can also be used to determine, e.g., if a set of devices is affected by a manufacturing defect.

While exemplary embodiments have been presented above, it should be appreciated that many variations exist.

Furthermore, while the description focuses in some areas on smartphones and smartwatches in exemplary embodiments, the teachings may be applied to various devices. It should also be appreciated that the exemplary embodiments are only examples, and are not intended to limit the scope, applicability, or configuration of the inventions in any way.

Information and signals disclosed herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof The various illustrative logical blocks, and algorithm steps described in connection with the embodiments disclosed herein may be implemented as electronic hardware, computer software, or combinations of both. To clearly illustrate this interchangeability of hardware and software, various illustrative components, blocks, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The techniques described herein may be implemented in hardware, software, firmware, or any combination thereof. Such techniques may be implemented in any of a variety of devices, such as, for example, wearable devices, wireless communication device handsets, or integrated circuit devices for wearable devices, wireless communication device handsets, and other devices. Any features described as devices or components may be implemented together in an integrated logic device or separately as discrete but interoperable logic devices. If implemented in software, the techniques may be realized at least in part by a computer-readable data storage medium comprising program code including instructions that, when executed, performs one or more of the methods described above. The computer-readable data storage medium may form part of a computer program product, which may include packaging materials. The computer-readable medium may comprise memory or data storage media, such as random access memory (RAM) such as synchronous dynamic random access memory (SDRAM), read-only memory, non-volatile random access memory (NVRAM), electrically erasable programmable read-only memory (EEPROM), flash memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

According to some embodiments, the techniques described herein are implemented by one or more special-purpose computing devices. The special-purpose computing devices may be hard-wired to perform the techniques, or may include digital electronic devices such as one or more application-specific integrated circuits (ASICs) or field programmable gate arrays (FPGAs) that are persistently programmed to perform the techniques, or may include one or more general purpose hardware processors programmed to perform the techniques pursuant to program instructions in firmware, memory, other storage, or a combination. Such special-purpose computing devices may also combine custom hard-wired logic, ASICs, or FPGAs with custom programming to accomplish the techniques. The special-purpose computing devices may be desktop computer systems, portable computer systems, handheld devices, networking devices, wearable devices, or any other device that incorporates hard-wired and/or program logic to implement the techniques.

Processor(s) in communication with (e.g., operating in collaboration with) the computer-readable medium (e.g., memory or other data storage device) may execute instructions of the program code, and may include one or more processors, such as one or more digital signal processors (DSPs), general purpose microprocessors, ASICs, FPGAs, or other equivalent integrated or discrete logic circuitry. Such a processor may be configured to perform any of the techniques described in this disclosure. A general purpose processor may be a microprocessor; but in the alternative, the processor may be any conventional processor, controller, microcontroller, or state machine. A processor may also be implemented as a combination of computing devices, for example, a combination of a DSP and a microprocessor, a plurality of microprocessors, one or more microprocessors in conjunction with a DSP core, or any other such configuration. Accordingly, the term "processor," as used herein may refer to any of the foregoing structure, any combination of the foregoing structure, or any other structure or apparatus suitable for implementation of the techniques described herein. Also, the techniques could be fully implemented in one or more circuits or logic elements.

The techniques of this disclosure may be implemented in a wide variety of devices or apparatuses, including a wearable device, a wireless handset, an integrated circuit (IC) or a set of ICs (e.g., a chip set). Various components, or units are described in this disclosure to emphasize functional aspects of devices configured to perform the disclosed techniques, but do not necessarily require realization by different hardware units. Rather, as described above, various units may be combined in a hardware unit or provided by a collection of inter-operative hardware units, including one or more processors as described above, in conjunction with suitable software and/or firmware.

Although the foregoing has been described in connection with various different embodiments, features, or elements from one embodiment may be combined with other embodiments without departing from the teachings of this disclosure. However, the combinations of features between the respective embodiments are not necessarily limited thereto.

What is claimed is:

1. A computer-implemented method, comprising:

receiving heart rate data of a user from a photoplethysmographic (PPG) sensor of a wearable device being worn by the user, the PPG sensor being positioned on a skin-side surface of the wearable device such that the PPG sensor is adjacent to skin of the user when being worn by the user;

receiving a set of fit data from a plurality of fit sensors of the wearable device, the plurality of fit sensors being spaced apart from each other and from the PPG sensor on the wearable device, the set of fit data being associated temporally with the heart rate data, the set of fit data being indicative of a contact force applied by the user at each of the plurality of fit sensors;

generating a fit signature using at least one of curve fitting techniques, finite element analysis, a predetermined relationship, or a look-up function on the set of fit data, the fit signature including an estimated contact force applied by the user at the PPG sensor, the fit signature being indicative of a fit of the wearable device on the user;

comparing the fit signature to a predetermined range;

presenting, when the fit signature is outside the predetermined range, a notification to the user via a display of the wearable device or an application on another device, the notification prompting the user to adjust a position of the wearable device;

designating, when the fit signature is outside the predetermined range, the heart rate data as a sub-optimal signal; and determining, when the fit signature is within the predetermined range, a heart rate of the user using the heart rate data.

2. A computer-implemented method, comprising:

receiving biometric data from a skin sensor of a wearable device;

receiving a set of fit data from a plurality of fit sensors of the wearable device, the plurality of fit sensors being spaced apart from each other and from the skin sensor on the wearable device, the set of fit data being associated temporally with the biometric data, the set of fit data being indicative of a contact force applied at each of the plurality of fit sensors;

generating a fit signature using at least one of curve fitting techniques, finite element analysis, a predetermined relationship, or a look-up function on the set of fit data, the fit signature including an estimated contact force applied at the skin sensor, the fit signature being indicative of a fit of the wearable device on a user;

comparing the fit signature to a predetermined range;

presenting, when the fit signature is outside the predetermined range, a notification to the user via a display of the wearable device, the notification prompting the user to adjust a position of the wearable device;

designating, when the fit signature is outside the predetermined range, the biometric data as a sub-optimal signal; and determining, when the fit signature is within the predetermined range, a biometric of the user using the biometric data.

3. The computer-implemented method of claim 2, further comprising:

controlling the skin sensor to stop collecting biometric data responsive to determining that the fit signature is outside the predetermined range; and controlling the skin sensor to resume collecting biometric data responsive to determining that the fit signature is within the predetermined range.

4. The computer-implemented method of claim 2, wherein the skin sensor is an optical sensor or an electrode-based sensor.

5. The computer-implemented method of claim 2, wherein the skin sensor is a photoplethysmographic (PPG) sensor or an electrocardiogram (ECG) sensor, a temperature sensor or a pulse oximeter (SpO2 sensor).

6. The computer-implemented method of claim 2, further comprising:

receiving one or more physiological metrics of the user, and wherein the predetermined range is based at least in part on the one or more physiological metrics of the user.

7. The computer-implemented method of claim 6, wherein the one or more physiological metrics of the user comprise one of a body mass index (BMI), age, sex, weight, wrist dimension, or body fat percentage.

8. The computer-implemented method of claim 2, wherein the plurality of fit sensors measures at least one of a force, a pressure, or a deflection of a housing of the wearable device.

9. The computer-implemented method of claim 8, wherein generating the fit signature comprises determining a pressure applied to the skin sensor.

10. The computer-implemented method of claim 9, further comprising:

calibrating the biometric data based at least in part on the pressure applied to the skin sensor; and recording the calibrated biometric data.

11. The computer-implemented method of claim 9, further comprising:

determining confidence scores for the biometric data, the confidence score based at least in part on the pressure applied to the skin sensor.

12. The computer-implemented method of claim 2, further comprising:

deleting, when the fit signature is outside the predetermined range, the biometric data.

13. The computer-implemented method of claim 2, further comprising:

determining that the wearable device is not being worn based on the fit signature being outside the predetermined range and based on at least one of data provided by the skin sensor, data provided by light sensors, data provided by inertial sensors, or learned user patterns.

14. A physiology measurement device, comprising:

a housing;

a skin sensor coupled to the housing, the skin sensor being configured to generate biometric data associated with a user when positioned adjacent skin of the user;

a plurality of fit sensors coupled to the housing, the plurality of fit sensors being spaced apart from each other and from the skin sensor on the housing, each respective fit sensor of the plurality of fit sensors being configured to generate fit data of a contact force applied at the respective fit sensor of the plurality of fit sensors;

a processor; and a memory device including instructions that, when executed by the processor, cause the memory device to:

receive the biometric data from the skin sensor, the biometric data associated with a time period;

receive a set of fit data from the plurality of fit sensors, the set of fit data associated with the time period;

generate a fit signature using at least one of curve fitting techniques, finite element analysis, or a look-up function on the set of fit data, the fit signature being indicative of an estimated contact force applied at the skin sensor, the fit signature being indicative of a fit of the physiology measurement device on the user;

compare the fit signature to a predetermined range;

present, when the fit signature is outside the predetermined range, a notification to the user; and designate, when the fit signature is outside the predetermined range, the biometric data as a sub-optimal signal.

15. The physiology measurement device of claim 14, wherein the instructions when executed by the processor, further cause the memory device to:

determine, when the fit signature is within the predetermined range, a biometric of the user using the biometric data.

16. The physiology measurement device of claim 14, wherein the skin sensor is a multi-wavelength optical sensor or an electrode-based sensor.

17. The physiology measurement device of claim 14, wherein the plurality of fit sensors are configured to measure a force, a pressure, or a deflection of the housing.

18. The physiology measurement device of claim 14, further comprising a display attached to the housing, wherein the notification is presented on the display.

19. The physiology measurement device of claim 14, wherein the instructions when executed by the processor, further cause the memory device to:

calculate a pressure applied to the plurality of fit sensors based on data provided by the plurality of fit sensors.

20. The physiology measurement device of claim 14, wherein the notification prompts the user to adjust a position of the physiology measurement device.

* * * * *